(12) United States Patent
Wang et al.

(10) Patent No.: US 12,254,684 B2
(45) Date of Patent: Mar. 18, 2025

(54) SMART DIAGNOSIS ASSISTANCE METHOD TO SOLVE RESULTS OF INACCURATE CLASSIFICATION OF IMAGE, AND TERMINAL BASED ON MEDICAL IMAGES

(71) Applicant: SHENZHEN INSTITUTES OF ADVANCED TECHNOLOGY CHINESE ACADEMY OF SCIENCES, Guangdong (CN)

(72) Inventors: Shuqiang Wang, Guangdong (CN); Wen Yu, Guangdong (CN); Yanyan Shen, Guangdong (CN); Zhuo Chen, Guangdong (CN)

(73) Assignee: SHENZHEN INSTITUTES OF ADVANCED TECHNOLOGY CHINESE ACADEMY OF SCIENCES, Guangdong (CN)

( * ) Notice: Subject to any disclaimer, the term of this patent is extended or adjusted under 35 U.S.C. 154(b) by 142 days.

(21) Appl. No.: 17/763,513

(22) PCT Filed: Nov. 19, 2019

(86) PCT No.: PCT/CN2019/119491
§ 371 (c)(1),
(2) Date: Mar. 24, 2022

(87) PCT Pub. No.: WO2021/097675
PCT Pub. Date: May 27, 2021

(65) Prior Publication Data
US 2022/0343638 A1    Oct. 27, 2022

(51) Int. Cl.
*G06V 10/80* (2022.01)
*G06T 7/00* (2017.01)
(Continued)

(52) U.S. Cl.
CPC ............ *G06V 10/82* (2022.01); *G06T 7/0012* (2013.01); *G06V 10/40* (2022.01); *G06V 10/764* (2022.01); *G06V 10/806* (2022.01); *G16H 30/40* (2018.01)

(58) Field of Classification Search
None
See application file for complete search history.

(56) References Cited

U.S. PATENT DOCUMENTS

| 7,680,307 B2 * | 3/2010 | Sathyanarayana .... G06F 18/254 |
| | | 382/128 |
| 2017/0344880 A1 | 11/2017 | Nekuii |

(Continued)

FOREIGN PATENT DOCUMENTS

| CN | 107578069 A | 1/2018 |
| CN | 107679572 A | 2/2018 |

(Continued)

OTHER PUBLICATIONS

International Search Report for PCT/CN2019/119491, Prepared by the China National Intellectual Property Administration, mailing date Jul. 29, 2020, 6 pages including the English Translation.

*Primary Examiner* — Haris Sabah
(74) *Attorney, Agent, or Firm* — Brooks Kushman P.C.

(57) ABSTRACT

The present application is suitable for use in the technical field of computers, and provides a smart diagnosis assistance method and terminal based on medical images, comprising: acquiring a medical image to be classified; pre-processing the medical image to be classified to obtain a pre-processed image; and inputting the pre-processed image into a trained classification model for classification processing to obtain a classification type corresponding to the pre-processed image, the classification model comprising tensorized network layers and a second-order pooling module. As the trained classification model comprises tensor decomposed (Continued)

network layers and a second-order pooling module, when processing images on the basis of the classification model, more discriminative features related to pathologies can be extracted, increasing the accuracy of medical image classification.

14 Claims, 6 Drawing Sheets

(51) Int. Cl.
  *G06V 10/40* (2022.01)
  *G06V 10/764* (2022.01)
  *G06V 10/82* (2022.01)
  *G16H 30/40* (2018.01)

(56) References Cited

U.S. PATENT DOCUMENTS

| | | | |
|---|---|---|---|
| 2019/0197368 | A1 | 6/2019 | Madani et al. |
| 2019/0311493 | A1* | 10/2019 | Hillborg ............... G06V 10/764 |
| 2019/0311814 | A1* | 10/2019 | Kannan ................. G16H 10/60 |
| 2019/0340752 | A1* | 11/2019 | Brestel .................. G16H 30/40 |
| 2019/0362835 | A1* | 11/2019 | Sreenivasan ........... G06N 3/044 |

FOREIGN PATENT DOCUMENTS

| | | |
|---|---|---|
| CN | 108198179 A | 6/2018 |
| CN | 108491874 A | 9/2018 |
| CN | 108961272 A | 12/2018 |

* cited by examiner

SMART DIAGNOSIS ASSISTANCE METHOD TO SOLVE RESULTS OF INACCURATE CLASSIFICATION OF IMAGE, AND TERMINAL BASED ON MEDICAL IMAGES

CROSS REFERENCE TO RELATED APPLICATIONS

This application is the U.S. national phase of PCT Application No. PCT/CN2019/119491 filed on Nov. 19, 2019, the disclosure of which IS incorporated in its entirety by reference herein.

TECHNICAL FIELD

The present application involves in the field of computer technologies, and particularly relates to a smart diagnosis assistance method based on medical images and a smart diagnosis assistance terminal based on medical images.

BACKGROUND

At present, with the development of society, performing smart assistance diagnosis for medical image classification based on a deep network model is applied more and more extensively. However, when a medical image is processed by a traditional deep network model, internal information of tissue structures and correlation information between different regions are lost, and the loss of the spatial structure information will eventually lead to an inaccurate classification result, thereby seriously affecting performance of a smart assistance diagnosis model for diseases.

SUMMARY

One of purposes of embodiments of the present application is to provide a smart diagnosis assistance method based on medical images and a smart diagnosis assistance terminal based on medical images, so as to solve the problem of the inaccurate classification result due to that a lot of internal structure information and internal correlation information of the image are lost when a medical image is processed by a traditional deep network model.

In order to solve the above technical problem, technical solutions adopted by the present application are as follows.

A first aspect provides a smart diagnosis assistance method based on medical images, which includes:

acquiring a medical image to be classified;

preprocessing the medical image to be classified to obtain a preprocessed image;

inputting the preprocessed image into a trained classification model for classification processing to obtain a classification category corresponding to the preprocessed image; here the classification model comprises a tensorized network layer and a second-order pooling module, the classification model is a ternary generative adversarial network obtained by training sample images and classification categories corresponding to the sample images based on a preset generator model, a preset discriminator model and a preset classifier model.

In an embodiment, in order to make the extracted global high-order feature map retain more important feature information, and thereby to improve the classification accuracy of the classification model, the inputting the preprocessed image into the trained classification model for classification processing to obtain the classification category corresponding to the preprocessed image includes:

normalizing the preprocessed image by using the classifier model to obtain a target image;

extracting key features in the target image by using the classifier model to obtain a global high-order feature map;

acquiring the classification category corresponding to the global high-order feature map by using the classifier model.

In an embodiment, in order to extract the global high-order feature map containing more feature information, the extracting the key features in the target image by using the classifier model to obtain the global high-order feature map includes:

extracting features in the target image through the tensorized network layer in the classifier model to obtain a first feature map;

performing channel dimension reduction on the first feature map through the second-order pooling module in the classifier model to obtain a dimension-reduced second feature map;

calculating a weight vector corresponding to the second feature map;

weighting the first feature map based on the weight vector to obtain the global high-order feature map.

In an embodiment, in order to improve the accuracy of the image classification, the present application further includes:

training the sample images and the classification categories corresponding to the sample images based on the preset generator model, the preset discriminator model and the preset classifier model to obtain the ternary generative adversarial network;

acquiring the trained classifier model from the ternary generative adversarial network.

In an embodiment, in order to improve the accuracy of the image classification and the speed of the classification, the training the sample images and the classification categories corresponding to the sample images based on the preset generator model, the preset discriminator model and the preset classifier model to obtain the ternary generative adversarial network includes:

generating a composite image label pair based on preset classification labels, a one-dimensional Gaussian random vector and the preset generator model;

predicting a sample image label pair corresponding to the sample image based on the sample image and the preset classifier model;

inputting the sample image label pair, a preset real image label pair and the composite image label pair into the preset discriminator model for discrimination processing to obtain a first discrimination result corresponding to the sample image label pair, a second discrimination result corresponding to the preset real image label pair and a third discrimination result corresponding to the composite image label pair;

calculating a first loss function corresponding to the preset generator model, a second loss function corresponding to the preset discriminator model and a third loss function corresponding to the preset classifier model based on the first discrimination result, the second discrimination result and the third discrimination result;

updating network parameters respectively corresponding to the preset generator model, the preset discriminator model and the preset classifier model through gradient descent of a backpropagation algorithm respectively based on the first loss function, the second loss function and the third loss function;

stopping training when the first loss function, the second loss function and the third loss function all converge to obtain the ternary generative adversarial network.

In an embodiment, in order to reduce the demand for medical images during training the network model, a composite image provided with a classification label may be generated through the preset generator model, and the generating the composite image label pair based on the preset classification labels, the one-dimensional Gaussian random vector and the preset generator model includes:

cascading the preset classification labels to the tensorized network layer, and generating the target feature map based on the one-dimensional Gaussian random vector;

enlarging the target feature map layer by layer based on the tensorized network layer to generate a target composite image;

generating the composite image label pair based on the target composite image and the preset classification labels.

In an embodiment, in order to improve the classification performance of the classification model, and thereby to improve the accuracy of the image classification, the inputting the sample image label pair, the preset real image label pair and the composite image label pair into the preset discriminator model for discrimination processing to obtain the first discrimination result corresponding to the sample image label pair, the second discrimination result corresponding to the preset real image label pair and the third discrimination result corresponding to the composite image label pair includes:

extracting feature information of the sample image label pair based on the tensorized dense convolutional neural network to obtain a sample feature map corresponding to the sample image label pair;

extracting feature information of the preset real image label pair based on the tensorized dense convolutional neural network to obtain a real feature map corresponding to the preset real sample image label pair;

extracting feature information in the composite image label pair based on the tensorized dense convolutional neural network to obtain a composite feature map corresponding to the composite image label pair;

performing discrimination processing on the sample feature map, the real feature map and the composite feature map respectively based on the preset discriminator model to obtain the first discrimination result, the second discrimination result and the third discrimination result.

A second aspect provides a smart diagnosis assistance terminal based on medical images, characterized in that, comprising:

an acquisition unit configured to acquire a medical image to be classified;

a preprocessing unit configured to preprocess the medical image to be classified to obtain a preprocessed image;

a classification unit configured to input the preprocessed image into a trained classification model for classification processing to obtain a classification category corresponding to the preprocessed image; here the classification model includes a tensorized network layer and a second-order pooling module, the classification model is a ternary generative adversarial network obtained by training sample images and classification categories corresponding to the sample images based on a preset generator model, a preset discriminator model and a preset classifier model.

Further, the classification unit includes:

a processing unit configured to normalize the preprocessed image by using the classifier model to obtain a target image;

an extraction unit configured to extract key features in the target image by using the classifier model to obtain a global high-order feature map;

a classification category acquisition unit configured to acquire the classification category Further, the extraction unit is specifically configured to:

extract features in the target image through the tensorized network layer in the classifier model to obtain a first feature map;

perform channel dimension reduction on the first feature map through the second-order pooling module in the classifier model to obtain a dimension-reduced second feature map;

calculate a weight vector corresponding to the second feature map;

weight the first feature map based on the weight vector to obtain the global high-order feature map.

Further, the terminal further comprises:

a training unit configured to train the sample images and the classification categories corresponding to the sample images based on the preset generator model, the preset discriminator model and the preset classifier model to obtain the ternary generative adversarial network;

a model acquisition unit configured to acquire the trained classifier model from the ternary generative adversarial network.

Further, the training unit comprises:

a generation unit configured to generate a composite image label pair based on preset classification labels, a one-dimensional Gaussian random vector and the preset generator model;

a determination unit configured to predict a sample image label pair corresponding to the sample image based on the sample image and the preset classifier model;

a discrimination unit configured to input the sample image label pair, a preset real image label pair and the composite image label pair into the preset discriminator model for discrimination processing to obtain a first discrimination result corresponding to the sample image label pair, a second discrimination result corresponding to the preset real image label pair and a third discrimination result corresponding to the composite image label pair;

a calculation unit configured to calculate a first loss function corresponding to the preset generator model, a second loss function corresponding to the preset discriminator model and a third loss function corresponding to the preset classifier model based on the first discrimination result, the second discrimination result and the third discrimination result;

an update unit configured to update network parameters respectively corresponding to the preset generator model, the preset discriminator model and the preset classifier model through gradient descent of a backpropagation algorithm respectively based on the first loss function, the second loss function and the third loss function;

a network generation unit configured to stop training when the first loss function, the second loss function and the third loss function all converge to obtain the ternary generative adversarial network.

The preset generator model includes the tensorized network layer.

Further, the generation unit is specifically configured to:

cascade the preset classification labels to the tensorized network layer, and generate the target feature map based on the one-dimensional Gaussian random vector;

enlarge the target feature map layer by layer based on the tensorized network layer to generate a target composite image;

generate the composite image label pair based on the target composite image and the preset classification labels.

The preset discriminator model includes a tensorized dense convolutional neural network.

Further, the discrimination unit is specifically configured to:

extract feature information of the sample image label pair based on the tensorized dense convolutional neural network to obtain a sample feature map corresponding to the sample image label pair;

extract feature information of the preset real image label pair based on the tensorized dense convolutional neural network to obtain a real feature map corresponding to the preset real sample image label pair;

extract feature information in the composite image label pair based on the tensorized dense convolutional neural network to obtain a composite feature map corresponding to the composite image label pair;

perform discrimination processing on the sample feature map, the real feature map and the composite feature map respectively based on the preset discriminator model to obtain the first discrimination result, the second discrimination result and the third discrimination result.

A third aspect provides another terminal, which includes a processor, an input device, an output device and a memory, the processor, the input device, the output device and the memory are mutually connected, here the memory is configured to store a computer program that supports a terminal to execute the foregoing method, the computer program includes a program instruction, and the processor is configured to invoke the program instruction to execute following steps of:

acquiring a medical image to be classified;

preprocessing the medical image to be classified to obtain a preprocessed image;

inputting the preprocessed image into a trained classification model for classification processing to obtain a classification category corresponding to the preprocessed image; here the classification model comprises a tensorized network layer and a second-order pooling module, the classification model is a ternary generative adversarial network obtained by training sample images and classification categories corresponding to the sample images based on a preset generator model, a preset discriminator model and a preset classifier model.

A fourth aspect provides a computer-readable storage medium, on which a computer program is stored, and the computer program, when executed by a processor, implements following steps of:

acquiring a medical image to be classified;

preprocessing the medical image to be classified to obtain a preprocessed image;

inputting the preprocessed image into a trained classification model for classification processing to obtain a classification category corresponding to the preprocessed image; here the classification model comprises a tensorized network layer and a second-order pooling module, the classification model is a ternary generative adversarial network obtained by training sample images and classification categories corresponding to the sample images based on a preset generator model, a preset discriminator model and a preset classifier model.

In the embodiments of the present application, the medical image to be classified is obtained through the terminal; the medical image to be classified is preprocessed to obtain the preprocessed image; and the preprocessed image is classified based on the trained classification model to acquire the corresponding classification result. Since the trained classification model includes the tensor-decomposited network layer and the second-order pooling module, the internal structure information and the internal correlation of the medical image are preserved when the medical image is processed based on this classification model, and the second-order pooling module, based on the dependencies of different regions of the medical image and the correlation information between different channels of high-order features, makes the weight of the important feature channel larger and the weight of the unimportant feature channel smaller under the action of the self-attention mechanism, so as to extract better discriminative features associated with a lesion, thereby improving the accuracy of the smart assistance diagnosis for diseases. Further, in the present application, the images are classified based on the ternary generative adversarial network, which, on the basis of the traditional binary generative adversarial network including a generator and a discriminator, adds up the classifier network model, and alleviates the problem of training instability of the binary generative adversarial network through designing a compatible loss function, solves the problem of inconsistent convergence points of the discriminator in the traditional binary generative adversarial network when performing two target tasks of distinguishing true and false and classifying, so that the generator model and the classifier model work in a cooperative training manner to replace the generative adversarial training method of the traditional binary generative adversarial network, thereby enabling the generator model and the classifier model to achieve the best optimality at the same time, speeding up the convergence, and making the generative adversarial network easier to reach the Nash equilibrium. In the present application, when the medical images are classified, the tensorization method instead of the traditional vectorization method is used to compress each network layer in the ternary generative adversarial network, which achieves the regularization effect on the network model while reducing the parameters, and solves the problems of excessive parameters and overfitting in classification and recognition of high-resolution images; further, the tensorization method can maintain internal correlation between the internal spatial structure information and different voxels, and solves the problem of information loss of the internal structure of the vectorized network layers. In the present application, the traditional first-order pooling (maximum pooling or average pooling) is replaced by the second-order pooling, and the better discriminative features are automatically extracted under the action of the self-attention mechanism by making full use of the second-order information of the overall image, thereby improving the classification accuracy of the classifier. The ternary generative adversarial network in the present application uses the semi-supervised learning method to jointly cooperate and train the preset generator model, the preset discriminator model and the preset classifier model, this reduces the network model's demand for image labeling information and makes full use of unlabeled data, thereby realizing the intelligent network model provided with high precision and high robustness; moreover, this reduces the number of the parameters, improves the computing efficiency, helps reduce the performance requirements of the terminal, thereby accelerating the disease diagnosis process for patients.

BRIEF DESCRIPTION OF THE DRAWINGS

In order to illustrate the technical solutions in the embodiments of the present application more clearly, the drawings needed to be used in description for the embodiments or exemplary technologies are briefly introduced below. Obviously, the drawings in the following description are only some embodiments of the present application, and other drawings may also be obtained for those of ordinary skill in the art based on these drawings without any creative effort.

DETAILED DESCRIPTION

Figure 1:
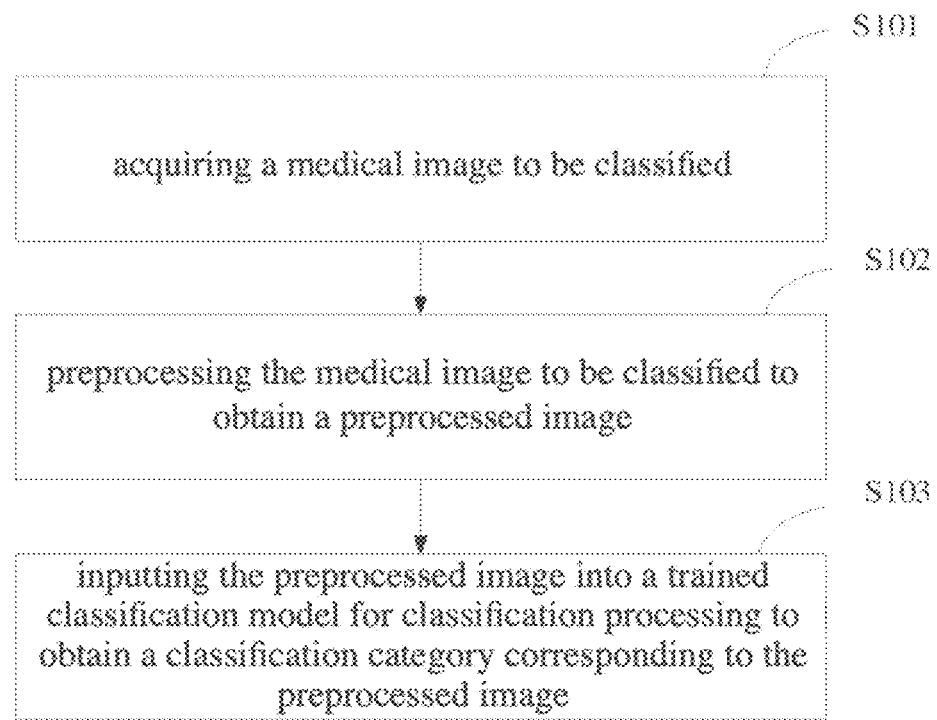
FIG. 1 is a flowchart of an implementation of a smart diagnosis assistance method based on medical images provided by an embodiment of the present application.

In order to make the purposes, technical solutions and advantages of the present application clearer and more comprehensible, the present application will be described in further detail below with reference to the accompanying drawings and embodiments. It should be understood that the specific embodiments described herein are only used to explain the present application, but not to limit the present application.

It should be noted that, when a component is referred to as being "fixed to" or "disposed on" another component, this component may be directly on the another component or indirectly on the another component; when a component is referred to as being "connected to" another component, this component may be directly or indirectly connected to the another component. Orientations or positional relationships indicated by the terms such as "upper", "lower", "left", "right" etc. are based on orientations or positional relationships as shown in the drawings, which are only intended to facilitate describing rather than to indicate or imply that a specified device or component must have a specific orientation or be constructed and operated in a specific orientation, and therefore cannot be understood as a limitation to the present application. The above terms may be understood according to specific situations for those of ordinary skill in the art. The terms "first" and "second" are only used for a descriptive purpose, and cannot be understood as an indication or implication of relative importance or an implicit indication of the number of a specified technical feature. The phrase "a plurality of" means two or more, unless otherwise explicitly and specifically defined.

In order to illustrate the technical solutions of the present application, a detailed description is given below with reference to the specific drawings and embodiments.

An embodiment of the present application provides a smart diagnosis assistance method based on medical images, which may be applied to classify medical images. The present application can efficiently process high-dimensional input data and at the same time ensure optimal classification performance, and thus is provided with strong practicability and extensibility. The present application is applicable to all disease classification tasks that can be diagnosed with medical images, for the convenience of description, the present application takes Alzheimer's disease as an example. Brain MRI (Magnetic Resonance Imaging) may be classified by this method, and the smart assistance diagnosis may be performed on the Alzheimer's disease according to classification results such as normal elderly, mild cognitive impairment and Alzheimer's disease. Specifically, based on a preset generator model, a preset discriminator model and a preset classifier model, sample images and classification categories corresponding to the sample images are trained to obtain a ternary generative adversarial network which includes a trained generator model, a trained discriminator model and a trained classifier model, and the MRI images are classified based on the trained classifier model to obtain corresponding classification results. Among them, the trained ternary generative adversarial network includes a tensor-decomposed network layer and a second-order pooling module.

In the present application, the images are classified based on the ternary generative adversarial network, which, compared with a traditional binary generative adversarial network, alleviates the problem of unstable training of the traditional generative adversarial network and solves the problem of inconsistent convergence points of the discriminator in the traditional binary generative adversarial network when performing two target tasks of distinguishing true and false and classifying. In the present application, when the images are classified, a tensorization method instead of a traditional vectorization method is used to compress each network layer in the ternary generative adversarial network, which achieves a regularization effect on the network model while reducing parameters, and solves the problems of excessive parameters and overfitting in classification and recognition of high-resolution images; further, the tensorization method can maintain internal correlation between the internal spatial structure information and different voxels, and solves the problem of internal structure loss of vectorized network layers. In the present application, the traditional first-order pooling (maximum pooling or average pooling) is replaced by second-order pooling, and better discriminative features are automatically extracted under the action of the self-attention mechanism by making full use of the second-order information of the overall image, thereby improving the classification accuracy of the classifier. The ternary generative adversarial network in the present application uses the semi-supervised learning method to jointly cooperate and train the preset generator model, the preset discriminator model and the preset classifier model, this reduces the network model's demand for image labeling information and makes full use of unlabeled data, thereby realizing the intelligent network model provided with high precision and high robustness; moreover, this reduces the number of parameters, improves the computing efficiency, helps reduce the performance requirements of the terminal, accelerates the speed of the medical image classification, and improves the disease diagnosis efficiency.

Please refer to FIG. 1. FIG. 1 is a schematic flowchart of a smart diagnosis assistance method based on medical images provided by an embodiment of the present application. An execution subject of the smart assistance diagnosis method in this embodiment is a terminal, and the terminal includes but is not limited to a mobile terminal such as a smart phone, a tablet computer, and a PDA (Personal Digital Assistant etc., and may also include a terminal such as a desktop computer etc. As shown in FIG. 1, the following may be included in the smart assistance diagnosis method.

At S101, acquire a medical image to be classified.

When detecting a medical image classification instruction, the terminal acquires the medical image to be classified. The medical image classification instruction is an instruction for instructing the terminal to perform medical image classification. The image classification instruction may be triggered by a user, for example, a doctor clicks on an image classification option in the terminal. The acquired medical image to be classified may be a medical image to be classified that is uploaded by the user to the terminal, or may be a medical image to be classified that is extracted by the terminal from a text file, here the terminal acquires the text file corresponding to the file identifier based on a file identifier included in the image classification instruction.

At S102, preprocess the medical image to be classified to obtain a preprocessed image.

The terminal preprocesses the medical image to be classified to obtain the preprocessed image. Specifically, the terminal processes the medical image to be classified into single-color channel images, and stitches the single-color channel images to obtain the preprocessed image. A single-color channel image is a color channel image composed of information including one kind of color elements. The channel that saves the color information of the image is called the color channel, and each color channel stores the information of the color elements in the image. For example, in a RGB color mode, R represents a red channel, G represents a green channel, and B represents a blue channel. The terminal may convert the channel mode of the medical image to be classified into a plurality of single-color channel images by invoking a preset function; and stitch the plurality of single-color channel images by invoking the preset function to obtain the preprocessed image.

At S103, input the preprocessed image into a trained classification model for classification processing to obtain a classification category corresponding to the preprocessed image. Here the classification model includes a tensorized network layer and a second-order pooling module; the classification model is a ternary generative adversarial network obtained by training sample images and classification categories corresponding to the sample images based on a preset generator model, a preset discriminator model and a preset classifier model.

The terminal inputs the preprocessed image into the trained classification model for classification processing, and obtains the classification category corresponding to the preprocessed image. The trained classification model is the ternary generative adversarial network obtained by training the sample images and the classification categories corresponding to the sample images based on the preset generator model, the preset discriminator model and the preset classifier model; the trained classification model includes the tensor-decomposed network layer and the second-order pooling module.

During the training, the preset generator model, the preset discriminator model and the preset classifier model cooperate with each other and work together to train the training data to obtain a trained ternary generative adversarial network. Here, the training data may include the sample images, the classification categories corresponding to the sample images (that is, preset real image labels), and unlabeled sample images. Specifically, the terminal generates composite images provided with classification labels based on preset classification labels, one-dimensional Gaussian random vectors, and the preset generator model, and finally generates composite image label pairs; acquires sample image label pairs corresponding to the sample images through prediction based on the sample images and the preset classifier model; inputs the sample image label pairs, the preset real image label pairs and the composite image label pairs into the preset discriminator model for discrimination to obtain a first discrimination result corresponding to the sample image label pairs, a second discrimination result corresponding to the preset real image label pairs and a third discrimination result corresponding to the composite image label pairs; calculates a first loss function corresponding to the preset generator model, a second loss function corresponding to the preset discriminator model and a third loss function corresponding to the preset classifier model based on the first discrimination result, the second discrimination result and the third discrimination result; updates network parameters respectively corresponding to the preset generator model, the preset discriminator model and the preset classifier model through gradient descent of a back-propagation algorithm based on the first loss function, the second loss function and the third loss function; stops the training when the first loss function, the second loss function and the third loss function are all converged to obtain the ternary generative adversarial network, that is, to obtain the trained classification model, here the trained classification model includes a trained generator model, a trained discriminator model and a trained classifier model. The preprocessed image is input into the trained classifier model, and the trained classifier model normalizes the preprocessed image to obtain a target image; the trained classifier model is used to extract key features in the target image to acquire a global high-order feature map; the trained classifier model obtains the classification category corresponding to the global high-order feature map and outputs the classification category, that is, the classification category corresponding to the preprocessed image is obtained.

Further, in order to make the extracted global high-order feature map retain more important feature information, and thereby improving the classification accuracy of the classification model, the S103 may include S1031, S1032 and S1033 specifically as follows.

At S1031, normalize the preprocessed image by using the classifier model to obtain a target image.

The trained classification model includes a trained generator model, a trained discriminator model and a trained classifier model, and the preprocessed image may be classified through the trained classifier model. Specifically, the preprocessed image is input into the trained classifier model, and the preprocessed image is normalized to obtain the target image. For example, data corresponding to the preprocessed image is acquired, and the data is transformed linearly so that voxel values corresponding to the preprocessed image are between $[-1, 1]$.

At S1032, extract key features in the target image by using the classifier model to obtain a global high-order feature map.

Figure 2:
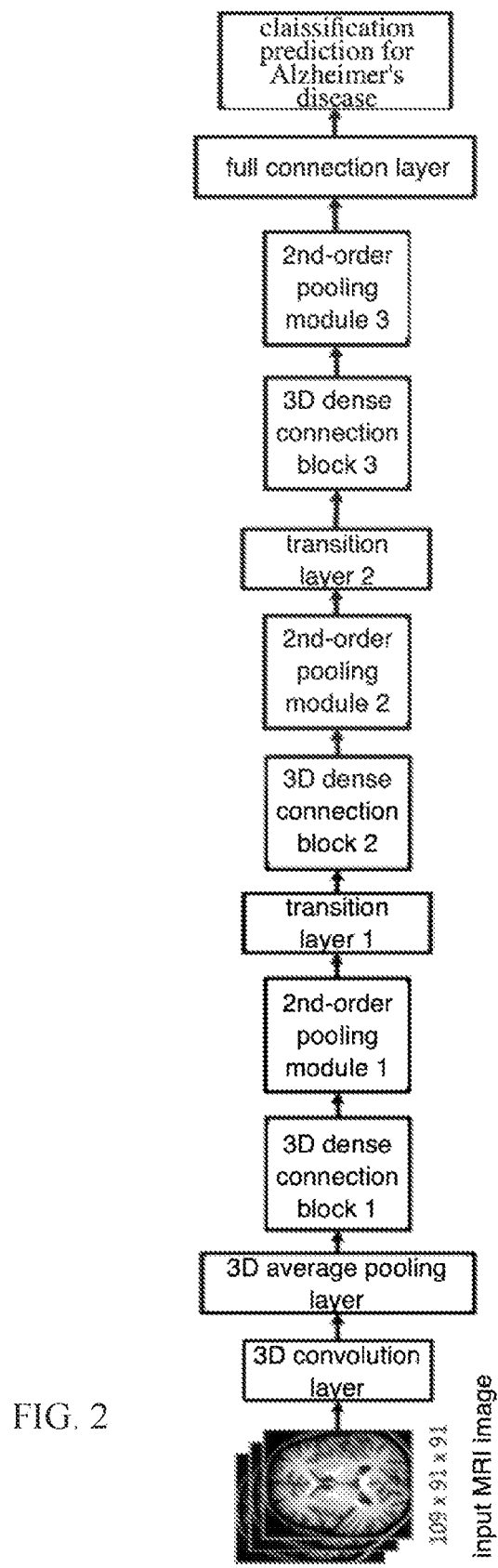
FIG. 2 is a structural schematic diagram of a trained classifier model provided by the present application.

The terminal extracts the key features in the target image by using the trained classifier model to obtain the global high-order feature map; and the trained classifier model includes a tensor-decomposited network layer and a second-order pooling module. Please refer to FIG. 2. FIG. 2 is a structural schematic diagram of the trained classifier model provided by the present application. As shown in FIG. 2, the trained classifier model includes a 3D convolution layer, a 3D average pooling layer, a 3D dense connection block 1, a second-order pooling module 1, a transition layer 1, a 3D dense connection block 2, a second-order pooling module 2, a transition layer 2, a 3D dense connection block 3, a second-order pooling module 3 and a full connection layer.

Specifically, during training the classification model, each network layer in the preset generator model, the preset discriminator model and the preset classifier model is tensorized. The classifier model is taken as an example, during the training, the network layers such as the 3D convolution layer, the 3D average pooling layer and the full connection layer etc. in the preset classifier model are tensorized. The terminal extracts the key features in the target image based on the tensor-decomposited network layers and the second-order pooling module in the trained classifier model to obtain the global high-order feature map.

In this embodiment, each network layer in the classifier model is tensorized, and each network layer in the classifier model is compressed by the tensorization method instead of the traditional vectorization method, which reduces parameters while achieving a regularization effect on the network model, thereby solving the problem of excessive parameters and overfitting in the classification and recognition of high-resolution images. In this embodiment, through replacing the traditional first-order pooling with the second-order pooling and taking full advantages of the second-order information of the input preprocessed image, and better discriminative features related to lesions are automatically extracted under the action of the self-attention mechanism, thereby improving the classification accuracy of the classifier; further, the classifier model uses the 3D convolution layer instead of a 2D convolution layer, so that the input image may be input in a form of tensor without any dimensionality reduction, thereby retaining the spatial information of the image and reducing the spatial information loss caused by the 2D network layer.

Further, in order to extract the global high-order feature map including more feature information, the S1032 may include S10321, S10322, S10323 and S10324 specifically as follows.

At S10321, extract features in the target image through the tensorized network layer in the classifier model to obtain a first feature map.

The terminal extracts the features in the target image through the tensorized network layer in the trained classifier model to obtain the first feature map. For example, the features in the target image are extracted through the 3D convolution layer, the 3D average pooling layer, etc. in the trained classifier model to obtain the first feature map.

At S10322, perform channel dimension reduction on the first feature map through the second-order pooling module in the classifier model to obtain a dimension-reduced second feature map.

Figure 3:
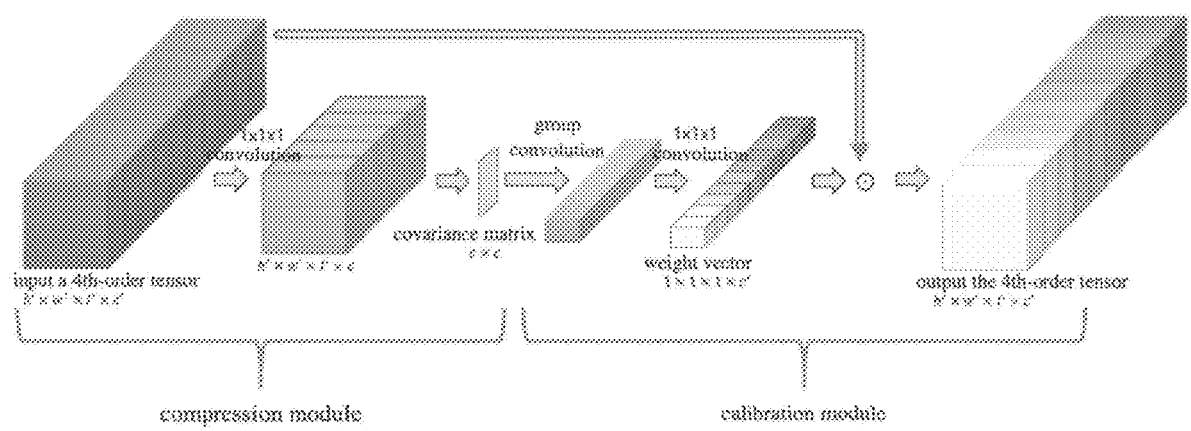
FIG. 3 is a structural schematic diagram of a second-order pooling module provided by the present application.

The terminal performs the channel dimension reduction on the first feature map through the second-order pooling module in the trained classifier model to obtain the dimension-reduced second feature map. Please refer to FIG. 3. FIG. 3 is a structural schematic diagram of the second-order pooling module provided by the present application, and the second-order pooling module includes a pre-shrinking module and a calibration module. Specifically, the channel dimension reduction is performed on the input four-dimensional feature map (i.e., the first feature map) through a 1×1×1 convolution to obtain the dimension-reduced second feature map.

At S10323, calculate a weight vector corresponding to the second feature map.

The terminal calculates the weight vector corresponding to the second feature map through the trained classifier model. Please refer to FIG. 3, specifically, covariance information of each two channels between different channels in the dimension-reduced second feature map is calculated to obtain a covariance matrix; and the weight vector having the same channel number with that of the four-dimensional feature map is acquired through a grouping convolution and the 1×1×1 convolution according to the covariance matrix.

At S10324, weight the first feature map based on the weight vector to obtain the global high-order feature map.

The terminal weights the first feature map based on the calculated weight vector, so that a weight of an important channel in the first feature map is larger and a weight of an unimportant channel is smaller, so as to obtain a more representative global high-order feature map. Specifically, the trained classifier model uses the back-propagation algorithm to make the weight of the important channel in the first feature map larger and the weight of the unimportant channel in the first feature map smaller, so as to extract more representative feature information and thus obtain the global high-order feature map.

At S1033, acquire the classification category corresponding to the global high-order feature map by using the classifier model.

The trained classifier model acquires the classification category corresponding to the global high-order feature map and outputs the classification category, that is, the classification category corresponding to the preprocessed image is acquired. Further, this classification category may be used to assist disease diagnosis in the embodiment of the present application, and the medical image to be classified is obtained through the terminal; the medical image to be classified is preprocessed to obtain the preprocessed image; and the preprocessed image is classified based on the trained classification model to acquire the corresponding classification result. Since the trained classification model includes the tensor-decomposed network layer and the second-order pooling module, the internal structure information and the internal correlation of the medical image are preserved when the medical image is processed based on this classification model, and the second-order pooling module, based on the dependencies of different regions of the medical image and the correlation information between different channels of high-order features, makes the weight of the important feature channel larger and the weight of the unimportant feature channel smaller under the action of the self-attention mechanism, so as to extract better discriminative features associated with a lesion, thereby improving the accuracy of the smart assistance diagnosis for diseases. Further, in the present application, the images are classified based on the ternary generative adversarial network, which, on the basis of the traditional binary generative adversarial network including a generator and a discriminator, adds up the classifier network model, and alleviates the problem of training instability of the binary generative adversarial network through designing a compatible loss function, solves the problem of inconsistent convergence points of the discriminator in the traditional binary generative adversarial network when performing two target tasks of distinguishing true and false and classifying, so that the generator model and the classifier model work in a cooperative training manner to replace the generative adversarial training method of the traditional binary generative adversarial network, thereby enabling the generator model and the classifier model to achieve the best optimality at the same time, speeding up the convergence, and making the generative adversarial network easier to reach the Nash equilibrium. In the present application, when the medical images are classified, the tensorization method instead of the traditional vectorization method is used to compress each network layer in the ternary generative adversarial network, which achieves the regularization effect on the network model while reducing the parameters, and solves the problems of excessive parameters and overfitting in classification and recognition of high-resolution images; further, the tensorization method can maintain internal correlation between the internal spatial structure information and different voxels, and solves the problem of internal structure loss of the vectorized network layers. In the present application, the traditional first-order pooling (maximum pooling or average pooling) is replaced by the second-order pooling, and the better discriminative features are automatically extracted under the action of the self-attention mechanism by making full use of the second-order information of the overall image, thereby improving the classification accuracy of the classifier. The ternary generative adversarial network in the present application uses the semi-supervised learning method to jointly cooperate and train the preset generator model, the preset discriminator model and the preset classifier model, this reduces the network model's demand for image labeling information and makes full use of unlabeled data, thereby realizing the intelligent network model provided with high precision and high robustness; moreover, this reduces the number of the parameters, improves the computing efficiency, helps reduce the performance requirements of the terminal, thereby accelerating the assistance diagnosis process.

Figure 4:
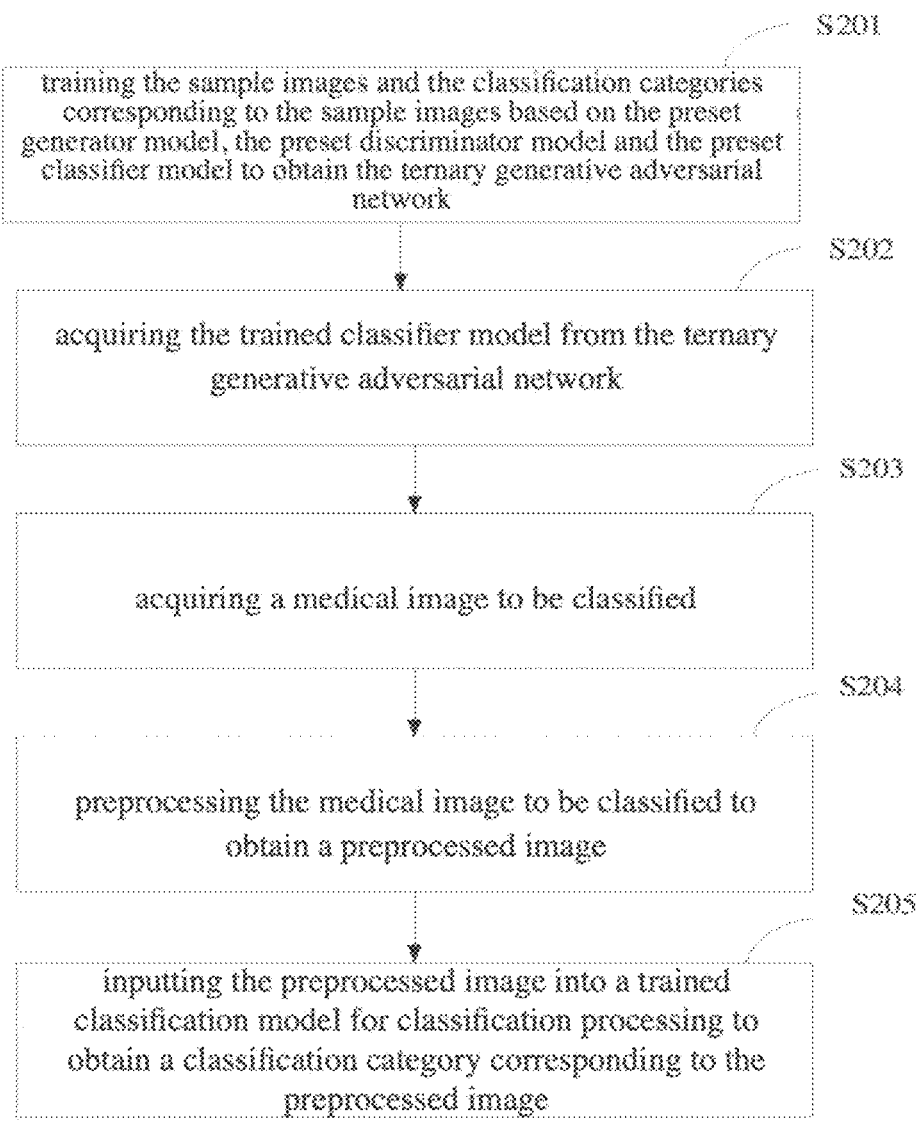
FIG. 4 is a flowchart of an implementation of a smart diagnosis assistance method based on medical images provided by another embodiment of the present application.

Please refer to FIG. 4. FIG. 4 is a schematic flowchart of a smart diagnosis assistance method based on medical images provided by another embodiment of the present application. An execution subject of the smart assistance diagnosis method in this embodiment is a terminal, and the terminal includes but is not limited to a mobile terminal such as a smart phone, a tablet computer, a personal digital assistant etc., and may also include a terminal such as a desktop computer.

On the basis of the previous embodiment, training steps S201 and S202 of the classifier model is added into this embodiment. S203, S204 and S205 in this embodiment are exactly the same as the S101, S102 and S103 in the previous embodiment, the details of which may refer to the relevant descriptions for the S101, S102 and S103 in the previous embodiment and will not be repeated herein. In order to improve the accuracy of image classification, the S201 and S202 of the smart assistance diagnosis method as shown in FIG. 4 are as follows:

At S201, train sample images and classification categories corresponding to the sample images based on the preset generator model, the preset discriminator model and the preset classifier model to obtain the ternary generative adversarial network.

Figure 5:
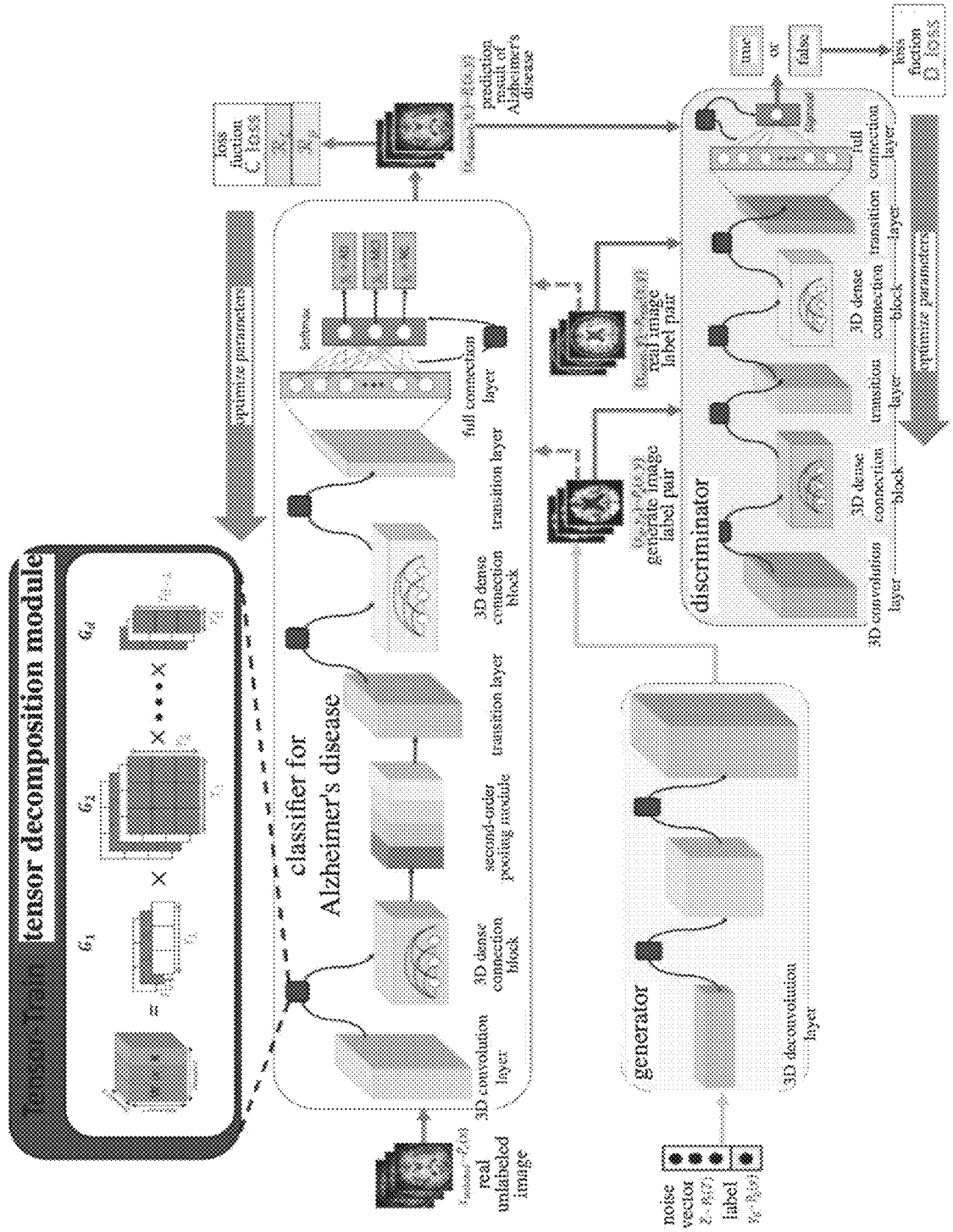
FIG. 5 is a structural schematic diagram of a ternary generative adversarial network provided by the present application.

Please refer to FIG. 5. FIG. 5 is a structural schematic diagram of the ternary generative adversarial network provided by the present application. Now, taking the application scenario of the Alzheimer's disease as an example, the processes of training and acquiring the ternary generative adversarial network are illustrated by combining the structure of the ternary generative adversarial network in FIG. 5. During the training, the generator in FIG. 5 refers to the preset generator model, and the corresponding trained generator model is generated after the training is completed; during the training, the discriminator in FIG. 5 refers to the preset discriminator model, and the corresponding trained discriminator model is generated after the training is completed; during the training, the Alzheimer's disease classifier in FIG. 5 refers to the preset classifier model, and the corresponding trained classifier model is generated after the training is completed. The preset generator model mainly includes a 3D deconvolution layer; the preset discriminator model mainly includes a 3D convolution layer, a 3D dense connection block, a transition layer, a full connection layer, etc.; the preset classifier model mainly includes a 3D convolution layer, a 3D dense connection block, a second-order pooling module, etc. It is worth noting that the Alzheimer's disease is only taken as an example here to train and acquire the smart assistance diagnosis model of Alzheimer's disease that can be used to classify MRI images; but classification models used for other medical images may be acquired by training trained through this method, which is not limited herein.

During the training, each network layer in the preset generator model, the preset discriminator model and the preset classifier model is tensorized. Specifically, parameter compression is performed on the 3D convolution layer and the full connection layer in the preset discriminator model and the preset classifier model and on the 3D deconvolution layer in the preset generator model through the tensor decomposition method; and a weight matrix of the full connection layer, a convolution kernel tensor of the deconvolution layer and a convolution kernel tensor of the convolution layer may all be expressed in a corresponding tensor form:

$$W((i_1,j_1)),\ldots,(i_d,j_d))=G_1[i_1,j_1]G_2[i_2,j_2]\ldots G_d[i_d,j_d].$$

Tensor decomposition is performed on the weight tensor W of the full connection layer according to the above formula to obtain a tensorized representation of the full connection layer as follows:

$$Y(i_1,\ldots,j_1))\Sigma_{j_1},\ldots,j_dG_1[i_1,j_1]G_2[i_2,j_2]\ldots G_d[i_d,j_d]X(j_1,\ldots,j_d)+B(i_1,\ldots,i_d).$$

Steps of the tensor decomposition of the 3D convolution layer and the deconvolution layer are as follows:

network input layer:

$$\chi(x, y, z, s) \xrightarrow{reshape} \tilde{\chi}(x, y, z, s_1, s_2, \ldots, s_d),$$

network output layer:

$$Y(x, y, z, s) \xrightarrow{reshape} \tilde{Y}(x, y, z, s_1, s_2, \ldots, s_d),$$

convolution kernel:

$$K(x, y, z, c, s) \xrightarrow{TT-format} G_0[i, j, k]G_1[c_1, s_1]\ldots G_d[c_d, s_d].$$

After the 3D convolution layer is tensorized, the following is obtained:

$$\tilde{Y}(x, y, z, s_1, \ldots, s_d) = \sum_{i=1}^{l}\sum_{j=1}^{l}\sum_{k=1}^{l}\sum_{c_1,\ldots,c_d} G_0[i, j, k]G_1[c_1, s_1]\ldots G_d[c_d, s_d]\tilde{\chi}$$
$$(i+x-1, j+y-1, k+z-1, c_1, \ldots, c_d)$$
$$\text{where } c = \prod_{i=1}^{d} c_i, s = \prod_{i=1}^{d} s_i.$$

During the training, the composite images provided with classification labels are generated based on the preset classification labels, the one-dimensional Gaussian random vectors and the preset generator model, and the composite image label pairs are finally generated; the sample image label pairs corresponding to the sample images are determined based on the sample images in the training data and the preset classifier model; the sample image label pairs, the preset real image label pairs and the composite image label pairs are input into the preset discriminator model for discrimination to obtain the first discrimination result corresponding to the sample image label pairs, the second discrimination result corresponding to the preset real image label pairs and the third discrimination result corresponding to the composite image label pairs; the first loss function corresponding to the preset generator model, the second loss function corresponding to the preset discriminator model and the third loss function corresponding to the preset classifier model are calculated based on the first discrimination result, the second discrimination result and the third discrimination result; the network parameters respectively corresponding to the preset generator model, the preset discriminator model and the preset classifier model are updated through gradient descent of the back-propagation algorithm based on the first loss function, the second loss function and the third loss function; and the training is stopped when the first loss function, the second loss function and the third loss function are all converged to obtain the ternary generative adversarial network, that is, to obtain the trained classification model. Here, the trained classification model includes the trained generator model, the trained discriminator model and the trained classifier model.

At S202, acquire the trained classifier model from the ternary generative adversarial network.

The trained classifier model is acquire from the ternary generative adversarial network. Specifically, the ternary generative adversarial network obtained by training is the trained classification model, and the trained classification model includes the trained generator model, the trained discriminator model and the trained classifier model, and the terminal acquires the trained classifier model from the trained classification model.

Further, in order to improve the accuracy of image classification and the speed of classification, in another embodiment, the S201 may include S2011, S2012, S2013, S2014, S2015 and S2016, which are specifically as follows.

At S2011, generate composite image label pairs based on preset classification labels, one-dimensional Gaussian random vectors, and the preset generator model.

Specifically, the one-dimensional Gaussian random vectors and the preset classification labels are used as input and are input into the preset generator model; the input preset classification labels are cascaded to each tensorized network layer through one-hot encoding, and the target feature map is generated based on the one-dimensional Gaussian random vectors; the target feature map is enlarged layer by layer based on the tensorized network layers, and the target composite image is finally generated; and thus the composite image label pairs are finally generated.

Further, in order to reduce the network model's demand for medical images, the semi-supervised learning method is introduced into the disease classification task, which can efficiently and comprehensively utilize the unlabeled medical image information, and at the same time the composite images provided with the classification labels are generated through the preset generator model, which plays a role of data enhancement and can train a high-precision assistance diagnosis model in a case of few number of samples. This reduces the demand for labeled training samples, reduces the workload of complicated labeling for training data in traditional algorithms, thereby further shortening the work period of disease diagnosis, accelerating the speed of disease diagnosis and improving the overall disease identification efficiency. The S2011 includes S20111, S20112 and S20113, which are as follows.

At S20111, cascade the preset classification labels to the tensorized network layers, and generate the target feature map based on the one-dimensional Gaussian random vectors.

The preset generator model includes tensorized network layers. For example, a tensorized deconvolution layer is included in the preset generator model. The input preset classification labels are cascaded to each tensorized deconvolution layer through the one-hot encoding, and the target feature map is generated based on the tensorized deconvolution layer and the one-dimensional Gaussian random vectors. Among them, an activation function of the deconvolution layer adopts a ReLU (Rectified Linear Unit) function and performs BN (Batch Normalization). In the assistance diagnosis and recognition of Alzheimer's disease, the target feature map is a anatomical brain feature map.

At S20112, enlarge the target feature map layer by layer based on the tensorized network layers to generate a target composite image.

After the plurality layers of deconvolution are performed, the tensorized network layers enlarge the target feature map layer by layer, and the obtained image is the target composite image. For example, the anatomical brain feature map is enlarged layer by layer to generate a composite image provided with the same size as a real MRI image. Here, a last layer of the preset generator model adopts a hyperbolic function, i.e., a tanh activation function.

At S20113, generate the composite image label pairs based on the target composite image and the preset classification labels.

The terminal generates the composite image label pairs based on the target composite image and the preset classification labels. For example, the terminal generates the MRI image provided with the classification label based on the composite image and the preset classification label. The MRI image provided with the classification label may also be referred to as an MRI image label pairs.

At S2012, predict sample image label pairs corresponding to the sample images based on the sample images and the preset classifier model.

The terminal predicts the corresponding category of the sample image based on the sample image in the training data and the preset classifier model, and determines the sample image label corresponding to the sample image based on the sample image and the corresponding category. Specifically, the sample image is input into the preset classifier model, the preset classifier model predicts the label information corresponding to the sample image and generates the sample image label pairs corresponding to the sample image based on the sample image and the label information. Taking the Alzheimer's disease as an example, the sample image is a real unlabeled MRI image, the real unlabeled MRI image is input into the preset classifier model, the preset classifier model predicts the label information corresponding to the real unlabeled MRI image and generates the MRI image label pairs based on the real unlabeled MRI image and the predicted label information.

At S2013, input the sample image label pair, the preset real image label pair, and the composite image label pair into the preset discriminator model for discrimination to obtain a first discrimination result corresponding to the sample image label pair, a second discrimination result corresponding to the preset real image label pair and a third discrimination result corresponding to the composite image label pair.

Specifically, the sample image label pair is input into the preset discriminator model for discrimination.

The preset discriminator model extracts the feature information of the sample image label pair to obtain the sample feature map corresponding to the sample image label pair, and the discrimination processing is performed on the sample feature map based on the preset discriminator model to obtain the first discrimination result. The preset real image label pair in the training data is input into the preset discriminator model for discrimination processing, and the preset discriminator model extracts the feature information of the preset real image label pair to obtain the real feature map corresponding to the preset real image label pair, and the discrimination processing is performed on the real feature map based on the preset discriminator model to obtain the second discrimination result. The composite image label pair is input into the preset discriminator model for discrimination processing, the preset discriminator model extracts the feature information of the composite image label pair to obtain the composite feature map corresponding to the composite image label pair, and the discrimination processing is performed on the composite feature map to obtain the third discriminant result.

Further, in order to improve the classification performance of the classification model and further improve the accuracy of the image classification, the S2013 may include S20131, S20132, S20133 and S20134, which are as follows.

At S20131, extract the feature information of the sample image label pair based on the tensorized dense convolutional neural network to obtain the sample feature map corresponding to the sample image label pair.

The preset discriminator model includes the tensorized dense convolutional neural network. The sample image corresponding to the sample image label pair is input into the preset discriminator model in a form of a third-order tensor, and the classification label in the sample image label pair, after one-hot encoded as a condition variable, is cascaded into each network layer of the preset discriminator model. Specifically, the tensorized dense convolutional neural network extracts the feature information of the sample image label pair to obtain the feature map that retains the spatial information, that is, to obtain the sample feature map corresponding to the sample image label pair. Here, the activation function of the convolution layer adopts ReLU and batch normalization.

At S20132, extract the feature information of the preset real image label pair based on the tensorized dense convolutional neural network to obtain the real feature map corresponding to the preset real sample image label pair.

The image corresponding to the real image label pair is input into the preset discriminator model in a form of a third-order tensor, and the classification label in the real image label pair, after one-hot encoded as a condition variable, is cascaded into each network layer of the preset discriminator model. Specifically, the tensorized dense convolutional neural network extracts the feature information of the real image label pair to obtain the feature map that retains the spatial information, that is, to obtain the real feature map corresponding to the real image label pair. Here, the activation function of the convolution layer adopts ReLU and batch normalization.

At S20133, extract the feature information in the composite image label pair based on the tensorized dense convolutional neural network to obtain the composite feature map corresponding to the composite image label pair.

The composite image is input into the preset discriminator model in a form of a third-order tensor, and the classification label corresponding to the composite image, after one-hot encoded as a condition variable, is cascaded into each network layer in the preset discriminator model. Specifically, the tensorized dense convolutional neural network extracts the feature information in the composite image label pair to obtain the feature map that retains the spatial information, that is, to obtain the composite feature map corresponding to the composite image label pair. Here, the activation function of the convolution layer adopts ReLU and batch normalization.

At S20134, perform discrimination processing on the sample feature map, the real feature map and the composite feature map respectively based on the preset discriminator model to obtain the first discrimination result, the second discrimination result and the third discrimination result.

Specifically, the preset discriminator model includes a tensorized full connection layer, and performs the discrimination based on a sigmoid function of the tensorized full connection layer to obtain the first discrimination result corresponding to the sample feature map, the second discrimination result corresponding to the real feature map and the third discrimination result corresponding to the composite feature map.

At S2014, calculate the first loss function corresponding to the preset generator model, the second loss function corresponding to the preset discriminator model and the third loss function corresponding to the preset classifier model based on the first discrimination result, the second discrimination result and the third discrimination result.

Specifically, during the process of training the preset generator model, the parameters of the tensor-decomposited kernel matrix $G_k[i_k,j_k]$ of the network layer in the preset generator model are updated in the backpropagation process according to the gradient descent of the loss function G-loss of the preset generator model. The goal of the preset generator model is to generate an image that can fool the preset discriminator model by simulating a real image. For example, the preset generator model generates a near-real MRI image that can fool the preset discriminator model by simulating real MRI anatomical brain structure features. Therefore, the loss of the preset generator model includes two parts, one part is to deceive the preset discriminator model to make the preset discriminator model discriminate the MRI image label pair generated by the preset generator model as true, and another part is reconstruction loss between the real MRI image and the generated MRI image, which may be expressed as:

$$\frac{\partial G - \text{loss}}{\partial G_k[i_k, j_k]} = \nabla_{\theta_g} \left[ \sum_{(x_g, y_g)} \log(1 - D(x_g, y_g)) + \lambda \|x_{label} - y_g\|_{L_1} \right].$$

During the process of training the preset discriminator model, the parameters of the tensor-decomposited kernel matrix $G_k[i_k,j_k]$ of the network layer in the preset discriminator model are updated in the backpropagation process according to the gradient descent of the loss function G-loss of the preset discriminator model. The goal of the preset discriminator model is to discriminate the real image label pair as true and discriminate the composite image label pair generated by the preset generator model and provided with the classification label as well as the image label pair predicted by the preset classifier model as false. For example, the goal of the preset discriminator model is to discriminate the real MRI image label pair as true and to discriminate the MRI image label pair generated by the preset generator model and the MM image label pair predicted by the preset classifier model as false. Therefore, the loss of the preset discriminator model includes three parts, which are specifically as follows:

$$\frac{\partial D - \text{loss}}{\partial G_k[i_k, j_k]}\Bigg|_{r_{k-1} \times r_k} = \nabla_{\theta_d} \begin{bmatrix} \sum_{(x_{label}, y)} \log D(x_{label}, y) + \\ \alpha \sum_{(x_{unlabel}, y_c)} \log(1 - D(x_{unlabel}, y_c)) + \\ (1 - \alpha) \sum_{(x_g, y_g)} \log(1 - D(x_g, y_g)) \end{bmatrix}$$

During the process of training the preset classifier model, the parameters of the tensor-decomposited kernel matrix $G_k[i_k, j_k]$ of the network layer in the preset classifier model are updated in the backpropagation process according to the gradient descent of the loss function G-loss of the preset classifier model. The goal of the preset classifier model is to automatically extract and classify the feature information in the preprocessed image, for example, to automatically extract MRI anatomical brain structure features for classification and classify the MRI image into one of three categories: normal, Alzheimer's disease and mild cognitive impairment. Therefore, the loss of the preset classifier model includes two parts, one part is supervised loss, that is, cross-entropy of the classification tasks performed on the real image and the generated image; another part is unsupervised loss, that is, the preset discriminator model is deceived to make the preset discriminator model discriminate the MRI image label pair which is generated by the preset classifier model for the unlabeled MRI image as true. Specifically, it may be expressed as:

$$\frac{\partial C - \text{loss}}{\partial G_k[i_k, j_k]} = \nabla_{\theta_c} [L_{supervised} + L_{unsupervised}],$$

$$L_{supervised} = R_L + \alpha_p R_p,$$

$$R_L = E_{(x_{label}, y) \sim P_{real}(x, y)} [-\log P_c(y \mid x_{label})],$$

$$R_p = E_{(x_g, y_g) \sim P_g(x, y)} [-\log P_c(y_g \mid x_g)],$$

$$L_{unsupervised} = E_{x_{unlabel} \sim P_c(x)} [\log(1 - D(x_{unlabel} C(x_{unlabel})))].$$

Calculation of $R_L$ for the real MRI image label pair is equivalent to calculation of KL divergence between distribution $P_c(x,y)$ learned by the preset classifier model and distribution $P_{real}(x,y)$ of the real data. The present generator model generates the MRI image label pair close to the real distribution, which can improve the classification performance of the classifier model, therefore, $R_P$ is P introduced to calculate the cross entropy of the generated MRI image label pair; minimization of $R_P$ is equivalent to minimization of the KL divergence $D_{KL}(P_g(x,y) \| P_c(x,y))$; since $R_P$ cannot be calculated directly, therefore the KL divergence $D_{KL}(P_g(x,y) \| P_c(x,y))$ cannot be calculated directly either, and the preset classifier model achieves the purpose of minimizing the KL divergence $D_{KL}(P_g(x,y)) \| P_c(x,y))$ through indirectly minimizing $R_P$.

At S2015, update network parameters respectively corresponding to the preset generator model, the preset discriminator model and the preset classifier model through gradient descent of a backpropagation algorithm respectively based on the first loss function, the second loss function and the third loss function.

The terminal updates the network parameters respectively corresponding to the preset generator model, the preset discriminator model and the preset classifier model through the gradient descent of the backpropagation algorithm respectively based on the calculated first loss function, second loss function and third loss function. For example, weight values etc. of each network layer in each of the preset generator model, the preset discriminator model and the preset classifier model are updated according to the first loss function, the second loss function and the third loss function. Then, the training is continued based on the parameter-updated preset generator model, preset discriminator model and preset classifier model. That is, the sample images and the classification categories corresponding to the sample images continue to be trained based on the respective parameter-updated models.

At S2016, stop training when the first loss function, the second loss function and the third loss function all converge, to obtain the ternary generative adversarial network.

The preset generator model, the preset discriminator model and the preset classifier model are cooperatively trained, such as repeatedly training in a cooperative mode of "generation-discrimination-classification". When the terminal detects that the first loss function, the second loss function and the third loss function have all converged during the training process that is in the repeated "generation-discrimination-classification" cooperative mode, the training is stopped, and then the trained ternary generative adversarial network is obtained, that is, the trained classification model. The number of iterations may also be preset, and it is considered that the training is completed when the training is performed up to this number of iterations, and the trained ternary generative adversarial network is obtained at this time.

In this embodiment of the present application, the medical image to be classified is obtained through the terminal; the medical image to be classified is preprocessed to obtain the preprocessed image; and the preprocessed image is classified based on the trained classification model to acquire the corresponding classification result. Since the trained classification model includes the tensor-decomposited network layer and the second-order pooling module, the internal structure information and the internal correlation of the medical image are preserved when the medical image is processed based on this classification model, and the second-order pooling module, based on the dependencies of different regions of the medical image and the correlation information between different channels of high-order features, makes the weight of the important feature channel larger and the weight of the unimportant feature channel smaller under the action of the self-attention mechanism, so as to extract better discriminative features associated with a lesion, thereby improving the accuracy of the smart assistance diagnosis for diseases. Further, in the present application, the images are classified based on the ternary generative adversarial network, which, on the basis of the traditional binary generative adversarial network including a generator and a discriminator, adds up the classifier network model, and alleviates the problem of training instability of the binary generative adversarial network through designing a compatible loss function, solves the problem of inconsistent convergence points of the discriminator in the traditional binary generative adversarial network when performing two target tasks of distinguishing true and false and classifying, so that the generator model and the classifier model work in a cooperative training manner to replace the generative adversarial training method of the traditional binary generative adversarial network, thereby enabling the generator model and the classifier model to achieve the best optimality at the same time, speeding up the convergence, and making the generative adversarial network easier to reach the Nash equilibrium. In the present application, when the medical images are classified, the tensorization method instead of the traditional vectorization method is used to compress each network layer in the ternary generative adversarial network, which achieves the regularization effect on the network model while reducing the parameters, and solves the problems of excessive parameters and overfitting in classification and recognition of high-resolution images; further, the tensorization method can maintain internal correlation of the image between the internal spatial structure information and different voxels, and solves the problem of internal structure loss of the vectorized network layers. In the present application, the traditional first-order pooling (maximum pooling or average pooling) is replaced by the second-order pooling, and the better discriminative features are automatically extracted under the action of the self-attention mechanism by making full use of the second-order information of the overall image, thereby improving the classification accuracy of the classifier. The ternary generative adversarial network in the present application uses the semi-supervised learning method to jointly cooperate and train the preset generator model, the preset discriminator model and the preset classifier model, this reduces the network model's demand for image labeling information and makes full use of unlabeled data, thereby realizing the intelligent network model provided with high precision and high robustness; moreover, this reduces the number of the parameters, improves the computing efficiency, helps reduce the performance requirements of the terminal, thereby improving the efficiency of the smart assistance diagnosis.

Figure 6:
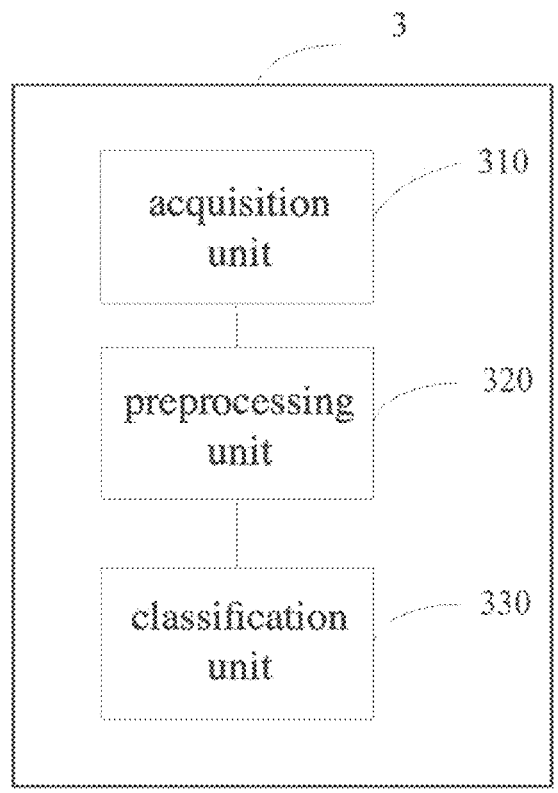
FIG. 6 is a schematic diagram of a smart diagnosis assistance terminal based on medical images provided by an embodiment of the present application.

Please refer to FIG. 6. FIG. 6 is a schematic diagram of a smart diagnosis assistance terminal based on medical images provided by an embodiment of the present application. The units included in this terminal is used to execute the steps in the embodiments corresponding to FIG. 1 and FIG. 4. For details, please refer to the relevant descriptions in the embodiments respectively corresponding to FIG. 1 and FIG. 4. For convenience of explanation, only the parts related to this embodiment are shown. Referring to FIG. 6, which includes:

an acquisition unit 310 configured to acquire a medical image to be classified;

a preprocessing unit 320 configured to preprocess the medical image to be classified to obtain a preprocessed image;

a classification unit 330 configured to input the preprocessed image into a trained classification model for classification processing to obtain a classification category corresponding to the preprocessed image; here the classification model includes a tensorized network layer and a second-order pooling module, the classification model is a ternary generative adversarial network obtained by training sample images and classification categories corresponding to the sample images based on a preset generator model, a preset discriminator model and a preset classifier model.

The trained classification model includes a trained classifier model.

Further, the classification unit 330 includes:

a processing unit configured to normalize the preprocessed image by using the classifier model to obtain a target image;

an extraction unit configured to extract key features in the target image by using the classifier model to obtain a global high-order feature map;

a classification category acquisition unit configured to acquire the classification category corresponding to the global high-order feature map by using the classifier model.

Further, the extraction unit is specifically configured to:

extract features in the target image through the tensorized network layer in the classifier model to obtain a first feature map;

perform channel dimension reduction on the first feature map through the second-order pooling module in the classifier model to obtain a dimension-reduced second feature map;

calculate a weight vector corresponding to the second feature map;

weight the first feature map based on the weight vector to obtain the global high-order feature map.

Further, the terminal further includes:

a training unit configured to train the sample images and the classification categories corresponding to the sample images based on the preset generator model, the preset discriminator model and the preset classifier model to obtain the ternary generative adversarial network;

a model acquisition unit configured to acquire the trained classifier model from the ternary generative adversarial network.

Further, the training unit includes:

a generation unit configured to generate a composite image label pair based on preset classification labels, a one-dimensional Gaussian random vector and the preset generator model;

a determination unit configured to predict a sample image label pair corresponding to the sample image based on the sample image and the preset classifier model;

a discrimination unit configured to input the sample image label pair, a preset real image label pair and the composite image label pair into the preset discriminator model for discrimination processing to obtain a first discrimination result corresponding to the sample image label pair, a second discrimination result corresponding to the preset real image label pair and a third discrimination result corresponding to the composite image label pair;

a calculation unit configured to calculate a first loss function corresponding to the preset generator model, a second loss function corresponding to the preset discriminator model and a third loss function corresponding to the preset classifier model based on the first discrimination result, the second discrimination result and the third discrimination result;

an update unit configured to update network parameters respectively corresponding to the preset generator model, the preset discriminator model and the preset classifier model through gradient descent of a backpropagation algorithm respectively based on the first loss function, the second loss function and the third loss function;

a network generation unit configured to stop training when the first loss function, the second loss function and the third loss function all converge to obtain the ternary generative adversarial network.

The preset generator model includes the tensorized network layer.

Further, the generation unit is specifically configured to:
cascade the preset classification labels to the tensorized network layer, and generate the target feature map based on the one-dimensional Gaussian random vector;
enlarge the target feature map layer by layer based on the tensorized network layer to generate a target composite image;
generate the composite image label pair based on the target composite image and the preset classification labels.

The preset discriminator model includes a tensorized dense convolutional neural network.

Further, the discrimination unit is specifically configured to:
extract feature information of the sample image label pair based on the tensorized dense convolutional neural network to obtain a sample feature map corresponding to the sample image label pair;
extract feature information of the preset real image label pair based on the tensorized dense convolutional neural network to obtain a real feature map corresponding to the preset real sample image label pair;
extract feature information in the composite image label pair based on the tensorized dense convolutional neural network to obtain a composite feature map corresponding to the composite image label pair;
perform discrimination processing on the sample feature map, the real feature map and the composite feature map respectively based on the preset discriminator model to obtain the first discrimination result, the second discrimination result and the third discrimination result.

Figure 7:
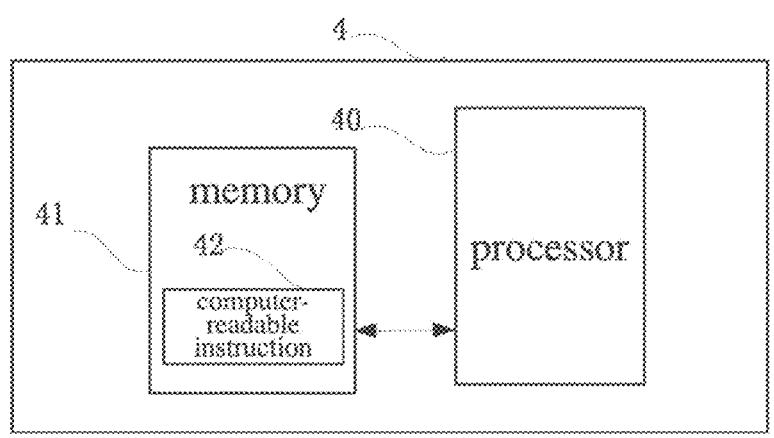
FIG. 7 is a schematic diagram of a terminal according to another embodiment of the present application.

Please refer to FIG. 7. FIG. 7 is a schematic diagram of a smart diagnosis assistance terminal based on medical images provided by another embodiment of the present application. As shown in FIG. 7, the terminal 4 of this embodiment includes: a processor 40, a memory 41, and a computer-readable instruction 42 stored in the memory 41 and executable on the processor 40. When executing the computer-readable instruction 42, the processor 40 implements the steps of the terminal in each of the embodiments of the smart diagnosis assistance method based on medical images, for example, the S101, S102 and S103 as shown in FIG. 1. Alternatively, when executing the computer-readable instruction 42, the processor 40 implements the functions of the units in the foregoing embodiments, for example, the functions of the units 310, 320 and 330 as shown in FIG. 6.

Exemplarily, the computer-readable instruction 42 may be divided into one or more units, and the one or more units are stored in the memory 41 and executed by the processor 40 to complete the present application. The one or more units may be a series of computer-readable instruction segments capable of completing specific functions, and the instruction segments are used to describe the execution process of the computer-readable instruction 42 in the terminal 4. For example, the computer-readable instruction 42 may be divided into an acquisition unit, a preprocessing unit, and a classification unit, and specific functions of the units are as described above.

The terminal may include, but is not limited to, the processor 40 and the memory 41. Those skilled in the art can understand that FIG. 7 is only an example of the terminal 4, and does not constitute a limitation on the terminal 4, which may include more or less components than those as shown in the figure, or combine some components or different components, for example the terminal may further include an input and output terminal, a network access terminal, a bus, and the like.

The so-called processor 40 may be a CPU (Central Processing Unit), and may also be other general-purpose processor, DSP (Digital Signal Processors), ASIC (Application Specific Integrated Circuit), FPGA (Field-Programmable Gate Array), or other programmable logic device, discrete gate or transistor logic device, discrete hardware component, etc. The general-purpose processor may be a microprocessor or the processor may be any conventional processor or the like.

The memory 41 may be an internal storage unit of the terminal 4, such as a hard disk or a storage of the terminal 4. The memory 41 may also be an external storage terminal of the terminal 4, such as a plug-in hard disk, a SMC (Smart Media Card), a SD (Secure Digital) card, flash card etc. equipped on the terminal 4. Further, the memory 41 may also include both an internal storage unit of the terminal 4 and an external storage terminal. The memory 41 is used to store the computer-readable instruction and other programs and data required by the terminal. The memory 41 may also be used to temporarily store data that has been output or will be output. The foregoing embodiments are only used to illustrate, but not to limit, the technical solutions of the present application; although the present application has been described in detail with reference to the foregoing embodiments, those of ordinary skill in the art should understand that: they can still modify the technical solutions described in the foregoing embodiments, or equivalently replace some technical features thereof; and these modifications or replacements do not make the essence of the corresponding technical solutions deviate from the spirit scope of the technical solutions of the embodiments of the present application, and should be included within the scope of protection of the present application.

What is claimed is:

1. A smart diagnosis assistance method based on medical images, comprising:
acquiring a medical image to be classified;
preprocessing the medical image to be classified to obtain a preprocessed image;
inputting the preprocessed image into a trained classification model for classification processing to obtain a classification category corresponding to the preprocessed image; wherein the classification model comprises a tensorized network layer and a second-order pooling module, the classification model is a ternary generative adversarial network obtained by training sample images and classification categories corresponding to the sample images based on a preset generator model, a preset discriminator model and a preset classifier model;
wherein, the trained classification model comprises a trained classifier model, and the inputting the preprocessed image into the trained classification model for classification processing to obtain the classification category corresponding to the preprocessed image comprises:
normalizing the preprocessed image by using the classifier model to obtain a target image;
extracting key features in the target image by using the classifier model to obtain a global high-order feature map;
acquiring the classification category corresponding to the global high-order feature map by using the classifier model;
wherein, the extracting the key features in the target image by using the classifier model to obtain the global high-order feature map comprises:

extracting features in the target image through the tensorized network layer in the classifier model to obtain a first feature map;

performing channel dimension reduction on the first feature map through the second-order pooling module in the classifier model to obtain a dimension-reduced second feature map;

calculating a weight vector corresponding to the second feature map;

weighting the first feature map based on the weight vector to obtain the global high-order feature map.

2. The smart diagnosis assistance method of claim 1, wherein, before acquiring the medical image to be classified, the method further comprises:

training the sample images and the classification categories corresponding to the sample images based on the preset generator model, the preset discriminator model and the preset classifier model to obtain the ternary generative adversarial network;

acquiring the trained classifier model from the ternary generative adversarial network.

3. The smart diagnosis assistance method of claim 2, wherein, the training the sample images and the classification categories corresponding to the sample images based on the preset generator model, the preset discriminator model and the preset classifier model to obtain the ternary generative adversarial network comprises:

generating a composite image label pair based on preset classification labels, a one-dimensional Gaussian random vector and the preset generator model;

predicting a sample image label pair corresponding to the sample image based on the sample image and the preset classifier model;

inputting the sample image label pair, a preset real image label pair and the composite image label pair into the preset discriminator model for discrimination processing to obtain a first discrimination result corresponding to the sample image label pair, a second discrimination result corresponding to the preset real image label pair and a third discrimination result corresponding to the composite image label pair;

calculating a first loss function corresponding to the preset generator model, a second loss function corresponding to the preset discriminator model and a third loss function corresponding to the preset classifier model based on the first discrimination result, the second discrimination result and the third discrimination result;

updating network parameters respectively corresponding to the preset generator model, the preset discriminator model and the preset classifier model through gradient descent of a backpropagation algorithm respectively based on the first loss function, the second loss function and the third loss function;

stopping training when the first loss function, the second loss function and the third loss function all converge to obtain the ternary generative adversarial network.

4. The smart diagnosis assistance method of claim 3, wherein, the preset generator model comprises the tensorized network layer, and the generating the composite image label pair based on the preset classification labels, the one-dimensional Gaussian random vector and the preset generator model comprises:

cascading the preset classification labels to the tensorized network layer, and generating the target feature map based on the one-dimensional Gaussian random vector, enlarging the target feature map layer by layer based on the tensorized network layer to generate a target composite image;

generating the composite image label pair based on the target composite image and the preset classification labels.

5. The smart diagnosis assistance method of claim 3, wherein, the preset discriminator model comprises a tensorized dense convolutional neural network;

wherein the inputting the sample image label pair, the preset real image label pair and the composite image label pair into the preset discriminator model for discrimination processing to obtain the first discrimination result corresponding to the sample image label pair, the second discrimination result corresponding to the preset real image label pair and the third discrimination result corresponding to the composite image label pair comprises:

extracting feature information of the sample image label pair based on the tensorized dense convolutional neural network to obtain a sample feature map corresponding to the sample image label pair;

extracting feature information of the preset real image label pair based on the tensorized dense convolutional neural network to obtain a real feature map corresponding to the preset real sample image label pair;

extracting feature information in the composite image label pair based on the tensorized dense convolutional neural network to obtain a composite feature map corresponding to the composite image label pair;

performing discrimination processing on the sample feature map, the real feature map and the composite feature map respectively based on the preset discriminator model to obtain the first discrimination result, the second discrimination result and the third discrimination result.

6. A smart diagnosis assistance terminal based on medical images, comprising a memory, a processor, and a computer-readable instruction stored in the memory and executable on the processor, wherein, the processor, when executing the computer-readable instruction, implements following steps of:

acquiring a medical image to be classified;

preprocessing the medical image to be classified to obtain a preprocessed image;

inputting the preprocessed image into a trained classification model for classification processing to obtain a classification category corresponding to the preprocessed image; wherein the classification model comprises a tensorized network layer and a second-order pooling module, the classification model is a ternary generative adversarial network obtained by training sample images and classification categories corresponding to the sample images based on a preset generator model, a preset discriminator model and a preset classifier model;

wherein the trained classification model comprises a trained classifier model, and the inputting the preprocessed image into the trained classification model for classification processing to obtain the classification category corresponding to the preprocessed image comprises:

normalizing the preprocessed image by using the classifier model to obtain a target image;

extracting key features in the target image by using the classifier model to obtain a global high-order feature map;

acquiring the classification category corresponding to the global high-order feature map by using the classifier model;

wherein the extracting the key features in the target image by using the classifier model to obtain the global high-order feature map comprises:

extracting features in the target image through the tensorized network layer in the classifier model to obtain a first feature map;

performing channel dimension reduction on the first feature map through the second-order pooling module in the classifier model to obtain a dimension-reduced second feature map;

calculating a weight vector corresponding to the second feature map;

weighting the first feature map based on the weight vector to obtain the global high-order feature map.

7. The terminal of claim 6, wherein before acquiring the medical image to be classified, the processor, when executing the computer-readable instruction, further implements following steps of:

training the sample images and the classification categories corresponding to the sample images based on the preset generator model, the preset discriminator model and the preset classifier model to obtain the ternary generative adversarial network;

acquiring the trained classifier model from the ternary generative adversarial network.

8. The terminal of claim 7, wherein, the training the sample images and the classification categories corresponding to the sample images based on the preset generator model, the preset discriminator model and the preset classifier model to obtain the ternary generative adversarial network comprises:

generating a composite image label pair based on preset classification labels, a one-dimensional Gaussian random vector and the preset generator model;

predicting a sample image label pair corresponding to the sample image based on the sample image and the preset classifier model;

inputting the sample image label pair, a preset real image label pair and the composite image label pair into the preset discriminator model for discrimination processing to obtain a first discrimination result corresponding to the sample image label pair, a second discrimination result corresponding to the preset real image label pair and a third discrimination result corresponding to the composite image label pair;

calculating a first loss function corresponding to the preset generator model, a second loss function corresponding to the preset discriminator model and a third loss function corresponding to the preset classifier model based on the first discrimination result, the second discrimination result and the third discrimination result;

updating network parameters respectively corresponding to the preset generator model, the preset discriminator model and the preset classifier model through gradient descent of a backpropagation algorithm respectively based on the first loss function, the second loss function and the third loss function;

stopping training when the first loss function, the second loss function and the third loss function all converge to obtain the ternary generative adversarial network.

9. The terminal of claim 8, wherein, the preset generator model comprises the tensorized network layer, and the generating the composite image label pair based on the preset classification labels, the one-dimensional Gaussian random vector and the preset generator model comprises:

cascading the preset classification labels to the tensorized network layer, and generating the target feature map based on the one-dimensional Gaussian random vector;

enlarging the target feature map layer by layer based on the tensorized network layer to generate a target composite image;

generating the composite image label pair based on the target composite image and the preset classification labels.

10. The terminal of claim 8, wherein, the preset discriminator model comprises a tensorized dense convolutional neural network;

wherein the inputting the sample image label pair, the preset real image label pair and the composite image label pair into the preset discriminator model for discrimination processing to obtain the first discrimination result corresponding to the sample image label pair, the second discrimination result corresponding to the preset real image label pair and the third discrimination result corresponding to the composite image label pair comprises:

extracting feature information of the sample image label pair based on the tensorized dense convolutional neural network to obtain a sample feature map corresponding to the sample image label pair;

extracting feature information of the preset real image label pair based on the tensorized dense convolutional neural network to obtain a real feature map corresponding to the preset real sample image label pair;

extracting feature information in the composite image label pair based on the tensorized dense convolutional neural network to obtain a composite feature map corresponding to the composite image label pair;

performing discrimination processing on the sample feature map, the real feature map and the composite feature map respectively based on the preset discriminator model to obtain the first discrimination result, the second discrimination result and the third discrimination result.

11. A non-transitory computer-readable storage medium, on which a computer program is stored, wherein, the computer program, when executed by a processor, implements following steps of:

acquiring a medical image to be classified;

preprocessing the medical image to be classified to obtain a preprocessed image;

inputting the preprocessed image into a trained classification model for classification processing to obtain a classification category corresponding to the preprocessed image; wherein the classification model comprises a tensorized network layer and a second-order pooling module, the classification model is a ternary generative adversarial network obtained by training sample images and classification categories corresponding to the sample images based on a preset generator model, a preset discriminator model and a preset classifier model;

wherein the trained classification model comprises a trained classifier model, and the inputting the preprocessed image into the trained classification model for classification processing to obtain the classification category corresponding to the preprocessed image comprises:

normalizing the preprocessed image by using the classifier model to obtain a target image;

extracting key features in the target image by using the classifier model to obtain a global high-order feature map;
acquiring the classification category corresponding to the global high-order feature map by using the classifier model;
wherein the extracting the key features in the target image by using the classifier model to obtain the global high-order feature map comprises:
extracting features in the target image through the tensorized network layer in the classifier model to obtain a first feature map;
performing channel dimension reduction on the first feature map through the second-order pooling module in the classifier model to obtain a dimension-reduced second feature map;
calculating a weight vector corresponding to the second feature map;
weighting the first feature map based on the weight vector to obtain the global high-order feature map.

12. The non-transitory computer-readable storage medium of claim 11, wherein before acquiring the medical image to be classified, the computer program, when executed by the processor, further implements following steps of:
training the sample images and the classification categories corresponding to the sample images based on the preset generator model, the preset discriminator model and the preset classifier model to obtain the ternary generative adversarial network;
acquiring the trained classifier model from the ternary generative adversarial network.

13. The non-transitory computer-readable storage medium of claim 12, wherein, the training the sample images and the classification categories corresponding to the sample images based on the preset generator model, the preset discriminator model and the preset classifier model to obtain the ternary generative adversarial network comprises:
generating a composite image label pair based on preset classification labels, a one-dimensional Gaussian random vector and the preset generator model;
predicting a sample image label pair corresponding to the sample image based on the sample image and the preset classifier model;
inputting the sample image label pair, a preset real image label pair and the composite image label pair into the preset discriminator model for discrimination processing to obtain a first discrimination result corresponding to the sample image label pair, a second discrimination result corresponding to the preset real image label pair and a third discrimination result corresponding to the composite image label pair;
calculating a first loss function corresponding to the preset generator model, a second loss function corresponding to the preset discriminator model and a third loss function corresponding to the preset classifier model based on the first discrimination result, the second discrimination result and the third discrimination result;
updating network parameters respectively corresponding to the preset generator model, the preset discriminator model and the preset classifier model through gradient descent of a backpropagation algorithm respectively based on the first loss function, the second loss function and the third loss function;
stopping training when the first loss function, the second loss function and the third loss function all converge to obtain the ternary generative adversarial network.

14. The non-transitory computer-readable storage medium of claim 13, wherein, the preset generator model comprises the tensorized network layer, and the generating the composite image label pair based on the preset classification labels, the one-dimensional Gaussian random vector and the preset generator model comprises:
cascading the preset classification labels to the tensorized network layer, and generating the target feature map based on the one-dimensional Gaussian random vector;
enlarging the target feature map layer by layer based on the tensorized network layer to generate a target composite image;
generating the composite image label pair based on the target composite image and the preset classification labels.

* * * * *